United States Patent [19]

Monthony et al.

[11] Patent Number: 5,091,316
[45] Date of Patent: Feb. 25, 1992

[54] BIOLOGICAL SAMPLE COLLECTION AND TRANSPORT DEVICE

[75] Inventors: James F. Monthony, Baltimore; David T. Stitt, Parkton; C. Michael Gosnell, Fallston, all of Md.; Shannon D. Stewart, Stewartstown, Pa.

[73] Assignee: Becton, Dickinson and Company, Franklin Lakes, N.J.

[21] Appl. No.: 508,506

[22] Filed: Apr. 11, 1990

Related U.S. Application Data

[63] Continuation of Ser. No. 346,142, May 4, 1989, abandoned, which is a continuation-in-part of Ser. No. 204,431, Jun. 9, 1988, abandoned.

[51] Int. Cl.$^5$ .............................................. C12M 1/30
[52] U.S. Cl. ........................................ 435/295; 604/1; 128/756
[58] Field of Search ................ 435/294, 295; 604/1-3; 128/756

[56] References Cited

U.S. PATENT DOCUMENTS

| | | | |
|---|---|---|---|
| 3,228,398 | 1/1966 | Leonard et al. | 604/1 |
| 3,394,702 | 7/1968 | Heimlich et al. | 604/1 |
| 3,508,547 | 4/1970 | Deuschle | 604/1 |
| 3,640,268 | 2/1972 | Davis | 604/1 |
| 3,724,018 | 4/1973 | Sills | 15/244 R |
| 3,783,106 | 1/1974 | Henshilwood | 435/295 |
| 3,871,375 | 3/1975 | Bennett | 604/1 |
| 3,877,464 | 4/1975 | Vermes | 604/1 |
| 4,014,748 | 3/1977 | Spinner et al. | 195/127 |
| 4,030,978 | 6/1977 | Abramson | 195/75 |
| 4,175,008 | 11/1979 | White | 435/295 |
| 4,223,093 | 9/1980 | Newman et al. | 435/295 |
| 4,311,792 | 1/1982 | Avery | 435/30 |
| 4,401,130 | 8/1983 | Halford et al. | 132/88.5 |

OTHER PUBLICATIONS

Stuart et al. "The Problem of Transport of Specimens for Culture of Gonococci", Can. J. Pub. Health; vol. 45; pp. 73-83 (1954).
C. K. Amies, "A Modified Formula for the Preparation of Stuart's Transport Medium", Can. J. Pub. Health; vol. 58; pp. 296-300 (1967).
Ellner et al. "Survival of Bacteria on Swabs", J. Bacteriol.; vol. 91; pp. 905-906) (1966).
Barry et al. "Efficiency of a Transport Medium for the Recovery of Aerobic and Anearobic Bacteria from Applicator Swab;" Appl. Microbiol.; vol. 24; pp. 31-33 (1972).
Ross et al. "Swabs and Swab-Transport Media Kits in the Isolation of Upper Respiratory Bacteria;" J. Clin. Pathol.; vol. 35; pp. 223-237 (1982).
Rubbo et al. "Some Observations on Survival of Pathogenic Bacteria on Cotton-Wool Swabs;" Brit. Med. J.; pp. 983-987 (May 1951).
K. F. Anderson, "Antibacterial Bacteriological Swabs;" Brit. Med. J.; pp. 1123-1124 (Nov. 1965).
Appelbaum et al., "Survival of Bacteria in Difco CultureSwab and Marion Culturette II Transport Systems;" J. Clin. Microbiol.; vol. 26; pp. 136-138 (1988).
Bach et al. "Inhibition of Microbial Growth by Fatty Amine Catalysts from Polyurethane Foam Test Tube Plugs;" Appl. Microbiol.; vol. 29, No. 5, pp. 615-620, May 1975.

Primary Examiner—Carroll B. Dority
Attorney, Agent, or Firm—Mary M. Allen; Nanette S. Thomas

[57] ABSTRACT

A microbiological culture collection and transport device maintains viable organisms for periods of time longer than possible with existing sampling devices. It also allows recovery of detectable antigen at levels not achievable with conventional swabs. The new device has a sterile swabbing tip made with a non-toxic polyurethane foam having open cells at its exposed surface. It does not require a transport medium and can be used dry. The device may further include a sample inoculator to distribute organisms collected onto a solid or semi solid medium. Methods for collecting and transporting microbiological specimens and for recovering detectable antigen are also described.

1 Claim, 1 Drawing Sheet

BIOLOGICAL SAMPLE COLLECTION AND TRANSPORT DEVICE

This application is a continuation of application Ser. No. 346,142, filed May 4, 1989, now abandoned, which is a continuation in part of Ser. No. 204,431, filed June 9, 1988, now abandoned.

FIELD OF THE INVENTION

The present invention relates to devices for collecting and transporting biological specimens. More particularly, it relates to an improved swab for collecting samples and a simplified transport device incorporating the improved swab.

BACKGROUND OF THE INVENTION

Detecting the presence of pathogenic microbial species requires, as a first step, collection of an appropriate sample. Typically a sterile collection device such as a swab is used. In the past, these swabs have been made of various materials such as cotton, sheep wool, polyester and rayon.

After the sample has been collected on a swab it is transported to a microbiology laboratory where any organisms present are identified. The identification method may be conventional culturing followed by identification or immunometric assay. A persistent problem for samples to be cultured has been maintaining viability of pathogenic organisms. Where the sample is to be processed for an immunoassay, a persistent problem has been recovery of immunologicaly active material. Additionally, the sample needs to be protected from contamination by the environment during transport. Numerous devices have been devised that provide both a means for obtaining the sample and means for protecting the sample during transport. Most often these devices comprise a swabbing element having a shaft typically of wood or plastic and a swabbing tip which has universally been produced from fibrous material such as cotton fibers, wool, polyester fibers or rayon fibers.

Further elements common to most devices are a cap to which the shaft is fixed and which mates with a lower swab cover to protect the swabbing tip both before and after collection of sample and a liquid medium containing reservoir such as a frangible glass ampoule that can be broken to release aqueous medium to keep the swab and sample moist. Representative collection and transport devices are shown in U.S. Pat. Nos. 4,223,093 (to Newman et al.), 4,030,978 (to Abramson), 4,175,008 (to White), 4,311,792 (to Avery), and 4,014,748 (to Spinner et al.).

Media described by Stuart et al. "The Problem of Transport of Specimens for Culture of Gonococci," *Can. J. Pub. Health*, vol. 45, pp. 73-83 (1954) and a later modification by Amies "A Modified Formula for the Preparation of Stuart's Transport Medium", *Can. J. Pub. Health*, vol. 58, pp. 296-300 (1967) are examples of growth maintenance media which do not promote growth that are commonly employed. Such media preserve the organisms present in the specimen while retarding or preventing growth during transport.

The medium is often retained inside the specimen collection device and adjacent to the specimen collection swabbing tip by an absorbent fibrous swatch of material. This swatch or pledget, as it is often named, can be a woven or non woven section of fabric or a piece of fibrous material such as cotton or rayon. While serving to restrain the flow of the aqueous media and prevent dehydration of the collected sample, the pledget materials such as cotton, polyester or rayon currently utilized do not enhance and may possibly be detrimental to preserving the viability of the microorganisms collected.

Several studies have attempted to evaluate the toxic nature of various fibrous materials used in the swab and also employed in the pledget. Studies are reported by Ellner et al. "Survival of Bacteria On Swabs", *J. Bacteriol.*, vol. 91, pp. 905-6 (1966); Barry et al. "Efficiency of a Transport Medium for the Recovery of Aerobic and Anaerobic Bacteria from Applicator Swabs," *Appl. Micro. Bio.*, vol. 24, pp. 31-3 (1972); Ross et al. "Swabs and Swab-Transport Media Kits in the Isolation of Upper Respiratory Bacteria," *J. Clin. Pathol.* vol. 35, pp. 223-7 (1982); Rubbo et al. "Some Observations on Survival of Pathogenic Bacteria on Cotton-Wool Swabs," *Brit. Med. J.*, pp. 983-7 (May 1951), and Anderson "Antibacterial Bacteriological Swabs", *Brit. Med. J.*, pp. 1123-4 (Nov. 1965).

Certain devices have eliminated the need for a liquid retaining pledget by substituting an agar containing medium for the liquid medium. The agar produces a gelled or highly viscous medium into which the specimen swab is placed after collecting the sample. The agar medium provides protection, but leads to agar residue on the swab. This residue can subsequently interfere with analytical procedures such as specimen staining for visual microscopic detection of organisms. Agar has also been found to interfere with certain latex agglutination tests commonly employed. Stuart et al. (cited above) have shown agar to be toxic to certain organisms.

A very recent study, Appelbaum, Peter C. et al., "Survival of Bacteria in Difco CultureSwab and Marion Culturette II Transport Systems," *J. Clin. Micro. Biol.*, vol. 26, pp. 136-8 (1988), typifies the commercial "state of the art" in describing two commonly available commercial systems with fibrous swabs and a media component. This study points out that 90% of the organisms cannot be recovered from either wet system after four hours storage time.

Devices having a liquid transport medium are expensive to make because they have multiple elements which must be formulated or made and then assembled. The devices with agar transport medium are less than acceptable because the agar interferes with subsequent testing. Thus, a substantial need exists for collection and transport devices that will yield viable organisms after four hours storage time.

The prior art clearly discourages the use of dry swabs. Similarly, it universally utilizes fibrous swabs of cotton, wool, rayon, polyester, and calcium alginate. Among the materials not previously used in swabs for collecting and transporting microorganism is polyurethane. At least one study, Bach, John A., et al., "Inhibition of Microbial Growth by Fatty Amine Catalysts from Polyurethane Foam Test Tube Plugs", *Appl. Micro. Biol.*, vol. 29 no. 5, pp. 615-620 (1975), has concluded that the material is not suitable for use when culturing microorganisms because autoclaving the polyurethane releases substances which are toxic to microorganisms.

Another acknowledgment that polyurethane may harm an organism with prolonged contact is found in U.S. Pat. No. 4,401,130 to Halford et al. That patent addresses the problem of joining a polyurethane foam swab to its stick without leaving dust which it characterizes as "possibly dangerous when open wounds are subject to treatment using the swabs." Col. 2, lines 27-8.

Polyurethane has been used in other health care applications. For example, one brand of contraceptive sponge is made from a special grade of polyurethane foam made from a foamable hydrophilic prepolymer resin available from W. R. Grace Co. and sold with the trademark Hypol. These resins are derived from toluene diisocyanate and methylenediphenyl diisocyanate. They have also been used in wound dressings. The polymers made from these resins are said to have no extractable toluene diamine, toluene diisocyanate, or other primary aromatic amines.

Polyurethane is recommended for use in a unitary molded swab described in U.S. Pat. No. 3,871,375. That patent states that the swab may be used for "application of medication, the removal of earwax, and all of the other uses for which swabs are normally employed." Col. 2, lines 16-18. It also states that the swab may be sterilized. It does not suggest use for collecting biological specimens and therefore does not address the known toxicity of polyurethane to microorganisms.

Additionally, polyurethane foam has been reported to be useful as a swab tip for removing foreign materials from a surface and to apply fluids such as paint, cosmetics, and medicines. U.S. Pat. No. 3,724,018 describes a swab made with a reticulated plastic foam material, such as polyurethane foam, wrapped around an end of a stick. The patent does not address sterilizing the swab or the known toxicity of polyurethane to microorganisms.

SUMMARY OF THE INVENTION

Surprisingly, many of the problems associated with existing devices are solved by using as the swabbing material a polyurethane foam which is non-toxic as demonstrated by a lack of a zone of growth inhibition when placed on a semi solid growth medium smeared with a suspension of *N. meningitidis* (Quality Control Collection, Becton Dickinson Microbioloqy Systems, ATCC 53900), *N. gonorrhoeae* (ATCC 19424) or *N. gonorrhoeae* (ATCC 43070) and which has open cells at its exposed surface. The new swab is comprised of a shaft and a sterile swabbing tip secured to one end of the shaft. The swabbing tip is formed with a polyurethane foam which is non-toxic as demonstrated by a lack of a zone of growth inhibition when placed on a semi-solid medium smeared with a suspension of *N. meningitidis* (Quality Control Collection, Becton Dickinson Microbioloqy Systems, ATCC 53900), *N. gonorrhoeae* (ATCC 19424) or *N. gonorrhoeae* (ATCC 43070) and which has open cells at its exposed surface.

This new swab can be used in a collection and transport device that is much simpler than existing devices. The new collection and transport device of the present invention comprises the new swab together with a cap secured to the end of the shaft opposite the swabbing tip and a tubular swab cover which covers the swab and mates with the cap to create a tortuous pathway and thereby to protect the swab from the environment. The collection and transport device may be free of any transport medium.

In a further aspect of the invention a sample inoculator is provided. Preferably the sample inoculator is secured to the exterior of the cap and a inoculator cover is provided to protect the inoculator from contamination prior to use.

DETAILED DESCRIPTION OF THE INVENTION

Figure 1:
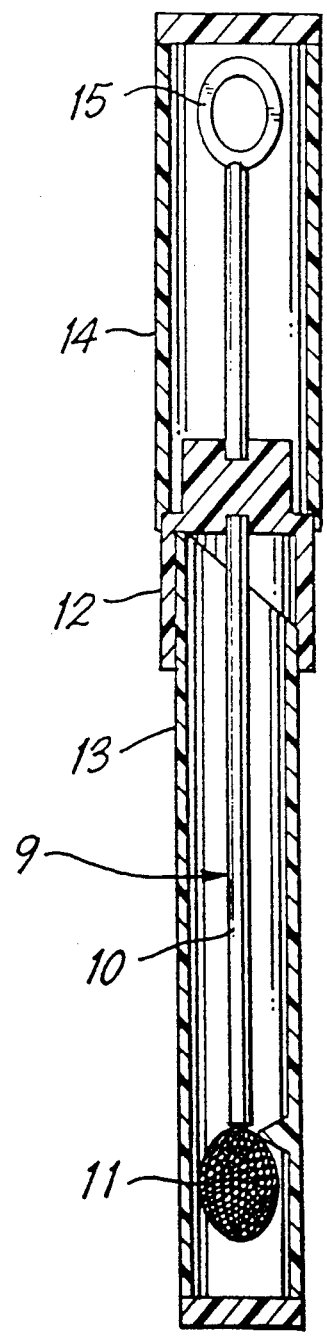
FIG. 1 shows the transport and collection device of the present invention.
Figure 2:
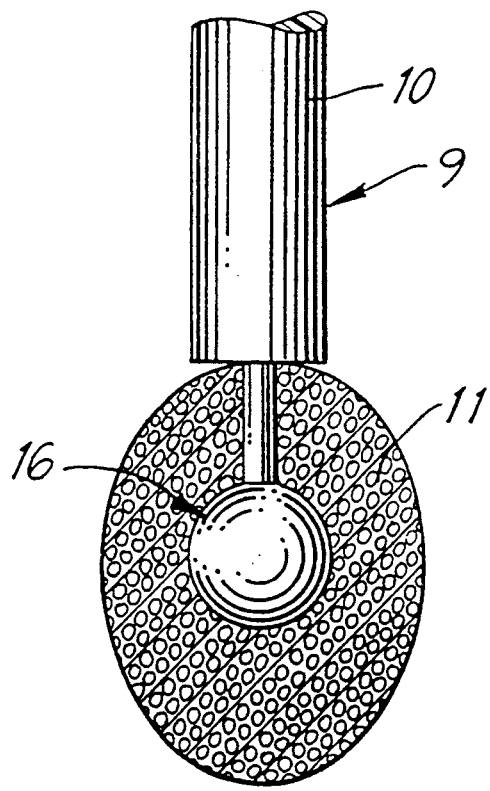
FIG. 2 shows a detail in cross section of the swabbing tip of the present invention.

As shown in the figures, the swab 9 of the present invention has a shaft 10 and a swabbing tip 11. The swab is secured to a cap 12 that mates with a swab cover 13 to form a slidable seal. An optional sample inoculator 15 is attached to cap 12 and protected by inoculator cover 14. While the inoculator is shown in an elliptical shape, those skilled in the art will appreciate that a variety of geometries can be used. For example, the inoculator could be formed as a cube or a tetrahedron.

The transport and collection device of the present invention does not require a liquid or solid transport medium. Elimination of these elements makes manufacture and assembly of the device much easier and therefore less expensive than manufacture and assembly of presently existing devices. The preferred foams used in the present invention can be sterilized with autoclaves opening up the possibility of using this sterilization procedure if appropriate materials are used for the remaining components of the transport device. The addition of sample inoculator 15 and inoculator cover 14 further enhances the usefulness of the device.

A variety of lengths and materials are possible for shaft 10 for example wood, plastic or wire might be utilized. Similarly the cap 12, swab cover 13, and sample inoculator 15 can be made of materials well known to those skilled in the art.

The advance of the present invention is use for the swabbing tip 11 of a sterile polyurethane foam which is non-toxic as demonstrated by a lack of a zone of growth inhibition when placed on a semi-solid growth medium smeared with a suspension of *N. meningitidis* (Quality Control Collection, Becton Dickinson Microbiology Systems, ATCC 53900), *N. gonorrhoeae* (ATCC 19424) or *N. gonorrhoeae* (ATCC 43070) and which has open cells on its exposed surface. Swabs which are found to be non-toxic to these three organisms after incubations on suitable semi solid growth media for twenty four, twenty four and forty eight hours respectively have been found to be non-toxic to a wide variety of human pathogens that are cultured from specimens collected with swabs and transported to the microbiology laboratory under conditions typically encountered by microbiologists. They have also been found to provide substantial improvement in recovery of materials that will participate in specific binding reactions in immunoassays.

The swabbing tip has open cells at its exposed surface which in use contacts the sampling site to collect the sample. The open cells at the surface may be achieved by using a reticulated foam or by using a non-reticulated foam and shearing the cells at the surface to create open cells. Preferably the foam has 20 to 200 pores per inch (8 to 80 pores per cm) at the surface and the cells fall within a size range of 0.0196 mm to 0.196 mm average diameter. Most preferably cells having an average diameter greater than 0.2 mm should be avoided. Shearing of a non-reticulated foam to create open cells at the surface may conveniently occur in a fabrication step whereby large blocks of foam are cut to size for attachment to the shaft. The swabbing tip 11 may have an inner core 16 to facilitate attachment and manufacture or may be attached directly to shaft 10.

The foam should be a medical grade foam substantially free of leachable monomers that can be toxic to microorganisms. Particularly preferred are foams sold under trade designations "SCOTFOAM Custom Foam", "SCOTFOAM Custom Foam CL", and "SCOTFOAM Special Pore-Custom Foam" having 60 to 100 pores per inch (24 to 40 pores per cm) in either pigmented or unpigmented form (all from SCOTFOAM Corp., Eddystone, Pa.).

The unexpected and unique ability of the polyurethane foam to maintain viable microorganisms without an aqueous medium and a pledget is most unexpected. Nothing in the prior art of microbiological swabs or polyurethane foams suggests that the polyurethane foam will provide a device that maintains the viability of microorganisms for periods equal or greater to the periods for which a medium wetted fiber swab can maintain such organism viability.

The unexpected benefits of the invention and other features of the invention will be appreciated from the following nonlimiting examples. In Examples 1 to 5 microorganisms used were obtained from the sources shown in Table I.

TABLE I

MICROORGANISM STRAINS UTILIZED

| CODE | TEST ORGANISM | SOURCE[a, b, c] |
|------|---------------|-----------------|
| CAL | Candida albicans | QCC, BDMS |
| ESC | Escherichia coli | ATCC 25922 |
| GCA | Neisseria gonorrhoeae | ATCC 19424 |
| GCB | Neisseria gonorrhoeae | ATCC 35201 |
| GCC | Neisseria gonorrhoeae | ATCC 43070 |
| HIA | Haemophilus influenzae | ATCC 35056 |
| HIB | Haemophilus influenzae | CI, JHH |
| NMA | Neisseria meningitidis | ATCC 53900 |
| NMB | Neisseria meningitidis | ATCC 13090 |
| PAA | Pseudomonas aeruginosa | ATCC 27853 |
| PRM | Proteus mirabilis | ATCC 12453 |
| SAC | Salmonella cholerasuis | ATCC 10708 |
| SGB | Streptococcus Group B | ATCC 10586 |
| SGD | Streptococcus Group D | ATCC 10541 |
| SHS | Shigella sonnei | ATCC 9290 |
| SPA | Streptococcus pyogenes | ATCC 10389 |
| SPB | Streptococcus pyogenes | QCC, BCMS |
| SNA | Streptococcus pneumoniae | ATCC 6305 |
| SNB | Streptococcus pneumoniae | CI, JHH |
| STA | Staphylococcus aureus | ATCC 25923 |
| VBP | Vibrio parahaemolyticus | QCC, BDMS |
| YRE | Yersinia enterocolitica | QCC, BDMS |

[a] ATCC = American Type Culture Collection
[b] QCC, BDMS = Quality Control Collection, Becton Dickinson Microbiology Systems, Cockeysville, MD 21030
[c] CI, JHH = Clinical Isolate, Johns Hopkins Hospital, Baltimore, MD.

COMPARATIVE EXAMPLE 1

The sterile swabbing tip made with a non-toxic polyurethane foam having open cells at its exposed surface and the simplified collection and transport device of the present invention were compared to commercially available products. Fastidious organisms used were Haemophilus influenzae, Neisseria meningitidis and Neisseria gonorrhoeae. The non-fastidious organisms Streptococcus pyogenes (Group A Strep) and Streptococcus pneumoniae were also studied. Two different strains of each fastidious and non-fastidious organisms, A and B, were studied. Table I identifies the actual strains and their sources. These organisms are all common potential human pathogens and are typical of the type of organism which may be sampled from a patient with a swab.

First the bacteria were grown in a broth culture medium. Then a suspension of each organism was diluted and its turbidity was measured in a spectrophotometer. The technique of quantitative plate counts was utilized to construct a graph relating the measured optical density to the number of organisms present. Thereafter, the number of organisms in a suspension was estimated by measurement of the optical density of the suspension and reading the concentration from the corresponding graph.

Suspensions were produced that contained approximately $5 \times 10^7$ colony forming units (CFU) per milliliter (ml). Each swab tested was inoculated by placing a 0.1 ml aliquot of the standard suspension in a sterile test tube, inserting the swab and allowing the aliquot to absorb into the swabbing tip.

In this experiment, swabs were from commercially available products, a rayon swab provided with the Culturette TM Collection and Transport System (Marion Scientific, Kansas City, Mo.) and a mini-size bonded polyurethane foam tip swab commonly sold for cleaning electronic surfaces (The Texwipe Co., Upper Saddle River, N.J. catalog no. TX710). These polyurethane swabs are made with a non reticulated foam which has open cells at its exposed surface. The rayon swabs were provided sterile. The polyurethane swabs were sterilized by gamma radiation prior to use. The inoculated rayon tipped swabs were returned to the transport tube and activated in accordance with the manufacturer's directions to bring the medium into contact with the pledget and swabbing tip. The inoculated polyurethane foam tipped swabs were placed individually in sterile screw capped plastic tubes. Multiple swabs were inoculated for streaking at the various time intervals.

Replicate samples of each type swab were stored aerobically at ambient temperatures. At timed intervals of 0, 4, 8, 24 or 48 hours, depending on the organism under study, the swab was used to inoculate a petri plate of an appropriate nutritive agar medium. Each inoculated plate was systematically streaked with a bacteriological loop according to the semi-quantitative "four quadrant method" commonly practiced by those skilled in the art of microbiology. Specifically, the plate was inoculated by:

A. Rolling the swab thoroughly over a first quadrant of the plate.

B. Using a standard bacteriological loop, streak back into quadrant 1 eight times.

C. Flame loop and streak back into quadrant 2 four times.

D. Streak back into quadrant 3 twice.

The inoculated plated media were incubated at 37° C. in an atmosphere enriched with 5% carbon dioxide. After twenty four to forty eight hours, the plates were observed for growth and graded according to the following scheme:

4 = Growth in quadrant 4 (20 to 100 colonies)
3 = Growth in quadrant 3 (20 to 100 colonies)
2 = Growth in quadrant 2 (20 to 100 colonies)
1 = Growth in quadrant 1 (20 to 100 colonies)
+ = Heavy growth (greater than 100 colonies)
− = Light growth (less than 20 colonies)

The results of this experiment are summarized in Table II (average score for duplicate runs). For each strain for each organism tested, use of the polyurethane swab demonstrated improved recovery of the organisms over that obtained from the rayon swab. Additionally, for 7 of 10 organisms studied the use of the polyurethane swab allowed recovery at time periods where the rayon swab showed no growth.

TABLE II

RECOVERY OF ORGANISMS FROM MARION CULTURETTE COLLECTION AND TRANSPORT DEVICE AND POLYURETHANE FOAM TIP SWABS

| Organism Strain | Swab Material | Recovery at Elapsed Storage Time (HR) | | | |
|---|---|---|---|---|---|
| | | 0 | 4 | 8 | 24 |
| HIA | Rayon | 3— | 1— | 0 | 0 |
| | Polyurethane | 4— | 3— | 2 | 1— |
| HIB | Rayon | 3 | 2— | 1 | 0 |
| | Polyurethane | 4— | 3 | 3— | 1+ |
| NMA | Rayon | 2 | 1— | 0 | 0 |
| | Polyurethane | 3— | 2+ | 2— | 1+ |
| NMB | Rayon | 4— | 1+ | 1— | 0 |
| | Polyurethane | 3— | 3— | 3— | 2 |
| GCA | Rayon | 2 | 0 | 0 | 0 |
| | Polyurethane | 3— | 1— | 1— | 0 |
| GCB | Rayon | 2— | 0 | 0 | 0 |
| | Polyurethane | 2— | 1 | 1— | 0 |
| SPA | Rayon | 2 | 1 | 0 | 0 |
| | Polyurethane | 2 | 2 | 2 | 1+ |
| SPB | Rayon | 3— | 2+ | 1+ | 1+ |
| | Polyurethane | 3— | 2+ | 3— | 2— |
| SNA | Rayon | 2 | 2— | 1 | 1+ |
| | Polyurethane | 3— | 3— | 3— | 3— |
| SNB | Rayon | 3— | 1+ | 1— | 1— |
| | Polyurethane | 3— | 2+ | 2— | 1 |

EXAMPLE 2

In this example, the sterile swabbing tip made with a non-toxic polyurethane foam having open cells at its exposed surface and the simplified collection and transport device of the present invention were compared to another commercially available sterile swabbing tip. The BBL Port-A-Cul ™ Aerobic Transport Device (Becton Dickinson Microbiology Systems, Cockeysville, Md.), has a rayon tipped swab, a rayon pledget and a medium following the formulation of Amies. The devices are sterilized by gamma radiation. After inoculation of the rayon swabs as in Example 1, the swabs were returned to the Port-A-Cul ™ device and activated according to the manufacturer's directions. The polyurethane swabs used and their method of inoculation and storage were as in Example 1. These tests were conducted with a similar panel of organisms as was used in Example 1. The results are shown in Table III (average score for duplicate runs). Here again a pattern of improved organism recovery through use of the polyurethane swabs over that obtained from the rayon swabs was observed. For some organisms, the use of the polyurethane swabs allowed recovery at time periods where the rayon swabs showed no growth.

TABLE III

RECOVERY OF ORGANISMS FROM BBL PORT-A-CUL AEROBIC TRANSPORT DEVICES AND POLYURETHANE FOAM TIP SWABS

| Organism Strain | Swab Material | Recovery at Elapsed Storage Time (HR) | | | |
|---|---|---|---|---|---|
| | | 0 | 4 | 8 | 24 |
| HIA | Rayon | 3— | 1— | 1— | 0 |
| | Polyurethane | 3— | 3— | 2+ | 2— |
| HIB | Rayon | 3 | 2— | 1 | 0 |
| | Polyurethane | 3— | 3— | 3— | 2 |
| NMA | Rayon | 3— | 1— | 0 | 0 |
| | Polyurethane | 3— | 3— | 2+ | 2— |
| NMB | Rayon | 4— | 2— | 1 | 0 |
| | Polyurethane | 4— | 4— | 3— | 2+ |

TABLE III-continued

RECOVERY OF ORGANISMS FROM BBL PORT-A-CUL AEROBIC TRANSPORT DEVICES AND POLYURETHANE FOAM TIP SWABS

| Organism Strain | Swab Material | Recovery at Elapsed Storage Time (HR) | | | |
|---|---|---|---|---|---|
| | | 0 | 4 | 8 | 24 |
| SPA | Rayon | 3 | 2+ | 2 | 2— |
| | Polyurethane | 3— | 2+ | 2 | 2— |
| SPB | Rayon | 3 | 3— | 2+ | 3— |
| | Polyurethane | 4— | 3 | 2+ | 3— |
| SNA | Rayon | 3— | 2+ | 2— | 1 |
| | Polyurethane | 3— | 3— | 2+ | 2 |
| SNB | Rayon | 3— | 2+ | 2— | 1 |
| | Polyurethane | 2 | 3— | 2— | 1 |

EXAMPLE 3

The sterile swabbing tip made with a non-toxic polyurethane foam having open cells at its exposed surface and the simplified collection and transport device of the present invention were compared again to a commercially available swabbing tip. The procedure followed and the commercially available rayon tip were identical to those of Example 2. The organisms were different. An additional 11 bacterial species and 1 yeast species were tested. The organisms are all potential human pathogens which can be collected from a patient using a swab collection and transport device. The results of this experiment are summarized in Table IV (average score for duplicate runs). With seven of eleven organisms studied, recovery from the polyurethane swab was equal to or better than that observed with the BBL Device, though recovery of all organisms was observed at 48 hours with both type swab sample devices.

TABLE IV

RECOVERY OF PATHOGENIC AND OPPORTUNISTIC ORGANISMS FROM BBL PORT-A-CUL AEROBIC TRANSPORT DEVICES AND POLYURETHANE FOAM TIP SWABS

| Organism Strain | Swab Material | Recovery at Elapsed Storage Time (HR) | | |
|---|---|---|---|---|
| | | 0 | 24 | 48 |
| PAA | Rayon | 3— | 3 | 4— |
| | Polyurethane | 3— | 4— | 3 |
| ESC | Rayon | 2 | 2+ | 2 |
| | Polyurethane | 3— | 3— | 3— |
| SAC | Rayon | 4— | 2 | 2— |
| | Polyurethane | 4 | 3 | 3+ |
| SHS | Rayon | 3— | 2+ | 2— |
| | Polyurethane | 4— | 3 | 2+ |
| PRM | Rayon | 4— | 3— | 2 |
| | Polyurethane | 4— | 3— | 3 |
| VBP | Rayon | 2 | 2— | 1— |
| | Polyurethane | 2 | 4— | 3— |
| YRE | Rayon | 2 | 2— | 2+ |
| | Polyurethane | 2 | 4— | 1+ |
| STA | Rayon | 4— | 3— | 2+ |
| | Polyurethane | 4— | 3— | 3+ |
| SGB | Rayon | 3 | 2+ | 3— |
| | Polyurethane | 3— | 3— | 2+ |
| SGD | Rayon | 3 | 3— | 2 |
| | Polyurethane | 3 | 3— | 2 |
| CAL | Rayon | 3 | 4— | 4— |
| | Polyurethane | 3 | 3— | 2+ |

EXAMPLE 4

In Examples 1, 2, and 3, the sterile swabbing tips made with a non toxic polyurethane foam having open cells at its exposed surface which were studied received no additional media after inoculation and during storage. In contrast, the rayon tipped swabs were moistened after activation in accordance with the instructions of their respective manufacturers. In this experiment, all of the swabs were stored in dry tubes. The polyurethane swabs were the same as those used in Examples 1, 2, and 3. Rayon tipped swabs were obtained from BBL Port-A-Cul TM devices (Becton Dickinson Microbiology Systems, Cockeysville, Md.) and from Culturette TM devices (Marion Scientific, Kansas City, Mo.). After inoculation, all rayon swabs were stored in the storage tube supplied by the manufacturer from which the fluid medium reservoir and pledget material were aseptically removed. Dacron tipped swab devices were obtained commercially from American Scientific Products (McGaw Park, Ill. catalog no. A5005-1). These swabs are provided sterile in a paper package.

Inoculation of all swabs in this experiment with *Streptococcus pyogenes* (Group A Streptococcus, SPA) was as in Example 1. Each inoculated rayon tipped swab was returned to its modified transport tube for storage. The polyurethane and Dacron swabs were placed individually in sterile screw capped tubes for storage. Additionally wet storage experiments were run by inoculating and activating swabs from Marion Culturette TM and BBL Port-A-Cul TM devices as in Examples 1 and 2.

The results of this experiment are summarized in Table V (average scores for duplicate runs). Organism recovery from polyurethane swabs, sterilized by three different methods, was better than that observed with either rayon or Dacron type swabs stored under similar dry conditions. Thus, enhanced recovery observed with the polyurethane swabs is related to type swab material and not method of storage or sterilization. Also, the use of polyurethane swabs again allowed recovery at time periods where rayon swabs, stored under moist or dry conditions, showed no growth.

TABLE 5

RECOVERY OF GROUP A STREPTOCOCCI FROM MOISTENED AND NON-MOISTENED SWAB DEVICES

| Swab Source | Swab Material | Storage Condition | Recovery at Elapsed Time (HR) | | |
|---|---|---|---|---|---|
| | | | 0 | 2 | 4 |
| Marion | Rayon | Moist | 3− | 2 | 0 |
| BBL | Rayon | Moist | ND[a] | ND | 2+ |
| BBL | Rayon | Dry | 3− | 0 | 0 |
| Scientific Prods. | Dacron | Dry | 3 | 1− | 1− |
| Texwipe | Polyurethane[b] | Dry | 3 | 3− | 2+ |
| | Polyurethane[c] | Dry | 3 | 3− | 3+ |
| | Polyurethane[d] | Dry | 3− | 3− | 2− |

[a]ND, not determined
[b]Sterilized by gamma radiation
[c]Sterilized by particle beam radiation
[d]Sterilized by ethylene oxide gas

EXAMPLE 5

This experiment was undertaken to demonstrate the beneficial effect of selecting as the swabbing tip a non-toxic polyurethane foam having open cells at its exposed surface. Several fastidious organisms were chosen to probe for toxic effects of the swabbing material.

Bacteria used in this experiment are as identified in Table I, and media used for growth and toxicity testing are as listed in Table VI. Each strain was grown overnight on the appropriate medium at 37° C. in an atmosphere enriched with 5% carbon dioxide. A suspension of each organism was then prepared in saline that contained approximately $1.5 \times 10^8$ cfu/ml. For each strain the surface of the toxicity testing medium indicated in Table 6 was systematically inoculated by a cross-streaked method, commonly practiced by those skilled in the art of microbiology, so as to produce confluent growth over the surface of the medium after incubation at 37° C. in an atmosphere enriched with 5% carbon dioxide. After each plate was so inoculated, swab tip materials were aseptically placed on the inoculated medium surface and plates were incubated as described above.

After twenty four hours incubation for strains NMA, NMB, and SPA and forty eight hours incubation for strains GCA and GCC, the plates were examined for a zone of growth inhibition about the swabbing tip material. The size of each zone of inhibition was measured and recorded in millimeters.

Rayon tipped swabs were obtained from Culturette TM devices (Marion Scientific, Kansas City, Mo.) and BBL Port-A-Cul TM devices (Becton Dickinson Microbiology Systems, Cockeysville, Md.). Polyurethane tipped swabs were obtained from two sources: The Texwipe Co., Upper Saddle River, N.J. (Catalog No. TX710)Catalog No. TX710) and Wilshire Foam Products, Inc., Carson City, Calif. (Catalog Nos. HT1001 and HT1005). The rayon swabs were provided sterile. The Texwipe and Wilshire HT1001 polyurethane swabs were sterilized with gamma radiation. The Wilshire HT1005 was asceptically used as supplied.

The results of this experiment are summarized in Table VII (average score for duplicate runs). These results serve to differentiate among polyurethane type materials. The preferred type polyurethane swabbing material should not be toxic. The Texwipe and Wilshire (H1001) are shown to be suitable for this purpose. Wilshire (H1005) was shown to be toxic to three of the five fastidious strains tested. For comparative purposes this experiment also demonstrates that differing sources of rayon swabbing materials may be differentiated relative to inherent toxicity.

TABLE VI

MEDIA USED FOR GROWTH AND TOXICITY TESTING

| ORGANISM TESTED | GROWTH MEDIUM (CATALOGUE NO.) | TOXICITY TEST MEDIUM (CATALOGUE NO.) |
|---|---|---|
| NMA | CHOC II AGAR (BDMS 21267)[a] | MUELLER HINTON II AGAR (BDMS 21800) |
| NMB | CHOC II AGAR (BDMS 21267) | MUELLER HINTON CHOC AGAR (BDMS 21802) |
| GCA | CHOC II AGAR (BDMS 21267) | MUELLER HINTON CHOC AGAR (BDMS 21802) |
| GCC | CHOC II AGAR (BDMS 21267) | MUELLER HINTON CHOC AGAR (BDMS 21802) |
| SPA | TSA II AGAR (BDMS 21261) | MUELLER HINTON II AGAR (BDMS 21800) |

[a]BDMS, Becton Dickinson Microbiology Systems, Cockeysville, MD.

TABLE VII

DETERMINATION OF TOXIC PROPERTIES OF POLYURETHANE AND RAYON SWABBING TIP MATERIALS

| Swab Source | Swab Material | Inhibition Zone Size (MM) | | | | |
|---|---|---|---|---|---|---|
| | | NMA | NMB | GCA | GCC | SPA |
| TEXWIPE | POLYURETHANE (#710) | 0 | 0 | 0 | 0 | 0 |
| WILSHIRE | POLYURETHANE (#1001) | 0 | 0 | 0 | 0 | 0 |
| WILSHIRE | POLYURETHANE (#1005) | 1 | 0 | 2 | 4 | 0 |
| MARION | RAYON | 6 | 0 | 0 | 1 | 0 |
| BBL | RAYON | 0 | 0 | 0 | 0 | 0 |

EXAMPLE 6

In this example, the ability to recover detectable Group A Streptococcal antigen was tested. Group A Streptococcus (*Streptococcus pyogenes*, ATCC 12385) was grown on blood agar plates for 24 hours at 37° C. A was adjusted with a spectrophotometer to obtain approximately $1 \times 10^9$ colony forming units (CFU) per milliliter (ml). Additional dilutions of this stock suspension were prepared in saline so as to contain in 0.050 ml $50 \times 10^5$, $12.5 \times 10^5$, $3.0 \times 10^5$, $1.5 \times 10^5$ and $0.75 \times 10^5$ CFU. A series of swabs were then inoculated by placing a 0.050 ml aliqout of suspension a sterile test tube, inserting the swab and allowing the aliquot to absorb into the swabbing tip. As a control for the assay system, swabs were also placed in tubes containing only 0.050 ml of saline before extraction. All swabs were tested in duplicate. Each set of duplicate swabs as well as the control swabs were assayed directly for Group A streptococcal antigen using the Directigen 1-2-3 TM Group A liposome immunoassay (Becton Dickinson Microbiology Systems, Cockeysville, Md.; cat. no. 8525-40). In this assay organisms are extracted from the swabs with nitrous acid, neutralized, and the resultant liquid extract is applied directly to a membrane containing antibody specific for Group A Streptococcus. Any Group A Streptococcus antigen present binds to the antibody. After washing, a suspension of liposomes having antibodies to Group A Streptococcus on their surface was applied to the membrane. The presence of antigen in the extracted material is detected by visually observing a pink triangle on the membrane surface. Intensely colored triangles were scored "reactive"; faintly colored triangles were scored as "minimally reactive"; and the absence of a visible triangle was scored as "non reactive".

Three of the four swabs tested in this experiment were commercially available products. A dacron Swab supplied with the Directigen 1-2-3 TM assay kit, the polyurethane swab available described in Example 1, and the polyurethane swab described in Example 5 (Wilshire Contamination Control, Carson, Calif.; catalog no. 1001). Also tested was an experimental swab manufactured by Wilshire Contamination Control using ScotFoam Special Pore-Custom Foam TM having 100 pores per inch (40 pores per cm) and white pigment. Each swab had an over all length of 6.0 in. (15.24 cm) and was comprised of a swabbing tip measuring about 0.625 in (1.59 cm) in length and 0.188 in. (0.48 cm) in diameter secured to a white polystyrene shaft of 0.094 in (0.238 cm) diameter. All polyurethane swabs were sterilized with gamma irradiation prior to use.

The results of this experiment are summarized in Table VIII (average of duplicate runs). In Table VIII "R" means reactive, "RM" means minimally reactive, "N" means non reactive, and "ND" means not determined. Group A streptococcal antigen was recoverable and detectable from foam swabs having one fourth the quantity of organisms of the least concentrated sample from which a detectable antigen could be recovered with the dacron swab. Thus when compared to the dacron swab utilized in the Directigen 1-2-3 TM test, the assay sensitivity was improved two to four fold.

TABLE VIII

RECOVERY OF GROUP A STREPTOCOCCUS ANTIGEN FROM DACRON AND POLYURETHANE FOAM TIP SWABS

| Swab Source | Swab Material | ORGANISM CONCENTRATION ($10^5$ CFU) | | | | | |
|---|---|---|---|---|---|---|---|
| | | 50 | 12.5 | 3.0 | 1.5 | 0.75 | 0 |
| Becton Dickinson | Dacron | R | R | N | N | N | N |
| Texwipe | Polyurethane (#710) | R | R | R | RM | N | N |
| Wilshire | Polyurethane (#1001) | R | R | R | RM | N | N |
| Wilshire | Polyurethane (experimental) | ND | R | RM | RM | RM | N |

What is claimed is:

1. A viable microorganism collecting and transporting device without transport media, comprising:
   a longitudinally extending sleeve container member comprising an open end, a closed end, and an inside and outside wall;
   a cap comprising an exterior and interior face being removably attachable to said open end and outside wall of said container;
   a shaft comprising a first and second end, wherein said first end is connected to said interior face of said cap;
   a swabbing tip connected to said second end of said shaft wherein said swab is made with a polyurethane foam which is specifically non-toxic to live microorganisms;
   said outside wall of said container member and said cap are longitudinally slidable relative to each other and form a slidable seal;
   a seal inoculator connected to said exterior end of said cap; and
   an inoculator cover removably attachable to said cap, to cover and protect the inoculator from contamination prior to use.

* * * * *

UNITED STATES PATENT AND TRADEMARK OFFICE
CERTIFICATE OF CORRECTION

PATENT NO. : 5,091,316
DATED : February 25, 1992
INVENTOR(S) : Monthony et al.

It is certified that error appears in the above-identified patent and that said Letters Patent is hereby corrected as shown below:

At column 3, line 43 delete "Microbiolocy" and insert -- Microbiology --.

At column 3, line 53 delete "Microbiolocy" and insert -- Microbiology --.

At column 5, line 17 delete "pledqet" and insert -- pledget --.

At column 5, line 46 delete "QCC, BCMS" and insert -- QCC, BDMS --.

At column 11, lines 23 and 24 delete "A was adjusted with a spectrophotometer" and insert -- A suspension was then prepared in saline and the turbidity was adjusted with a spectrophotometer --.

At column 12, line 56, Claim 1 delete "seal" and insert -- sample --.

Signed and Sealed this

Fifteenth Day of February, 1994

Attest:

BRUCE LEHMAN

*Attesting Officer*  *Commissioner of Patents and Trademarks*